(12) United States Patent
Meola

(10) Patent No.: US 10,799,645 B2
(45) Date of Patent: Oct. 13, 2020

(54) DOSAGE LIMITING DEVICE

(71) Applicant: Paul Meola, St. Petersburg, FL (US)

(72) Inventor: Paul Meola, St. Petersburg, FL (US)

( * ) Notice: Subject to any disclaimer, the term of this patent is extended or adjusted under 35 U.S.C. 154(b) by 224 days.

(21) Appl. No.: 16/011,772

(22) Filed: Jun. 19, 2018

(65) Prior Publication Data

US 2019/0381250 A1    Dec. 19, 2019

(51) Int. Cl.
*A61M 5/315* (2006.01)
*A61M 5/31* (2006.01)

(52) U.S. Cl.
CPC .... *A61M 5/31563* (2013.01); *A61M 5/31525* (2013.01); *A61M 5/31578* (2013.01); *A61M 5/3148* (2013.01); *A61M 2005/3125* (2013.01)

(58) Field of Classification Search
CPC .......... A61M 5/31563; A61M 5/31525; A61M 5/3148; A61M 2005/3125; A61M 2005/3114; A61M 2005/3022; A61M 5/31501; A61M 2005/31508; A61M 5/008; A61M 5/3137; A61M 5/315; A61M 2005/1586; A61M 2005/244; A61M 5/1418; A61M 5/3156; B01L 9/06
See application file for complete search history.

(56) References Cited

U.S. PATENT DOCUMENTS

| | | | | |
|---|---|---|---|---|
| 2,375,711 A | * | 5/1945 | Vondrak | A61M 5/3156 604/210 |
| 4,563,178 A | * | 1/1986 | Santeramo | A61M 5/1782 141/27 |
| 5,115,816 A | * | 5/1992 | Lee | A61M 5/1782 600/562 |
| 6,375,006 B1 | * | 4/2002 | Samuels | A61M 25/002 206/210 |
| 2012/0059347 A1 | * | 3/2012 | Freed | A61M 5/3129 604/500 |
| 2015/0196714 A1 | * | 7/2015 | Creaturo | A61M 5/3129 604/198 |
| 2019/0380913 A1 | * | 12/2019 | Meola | A61M 5/31501 |

* cited by examiner

*Primary Examiner* — Nathan R Price
*Assistant Examiner* — Melissa A Snyder
(74) *Attorney, Agent, or Firm* — Larson & Larson, P.A.; Frank Liebenow; Justin P. Miller

(57) ABSTRACT

A dosage limiting device is includes an elongated connecting member that has a plunger receiving head at a first end for capturing a plunger flange of a plunger of a syringe. The plunger receiving head has a back flange connected to the elongated connecting member and a forward slotted flange connected to the elongated connecting member, the forward slotted flange is separated from the back flange by a space sufficient to accept the plunger flange and a flat section of the plunger fitting in a slot of the forward slotted flange. A barrel loop is at a distal second end of the elongated connecting member so that the dosage limiting device limits a dosage provided by the syringe based upon a distance between the plunger receiving head and the barrel loop as the barrel loop abuts a barrel flange of the syringe, thereby limiting extraction of the plunger.

13 Claims, 7 Drawing Sheets

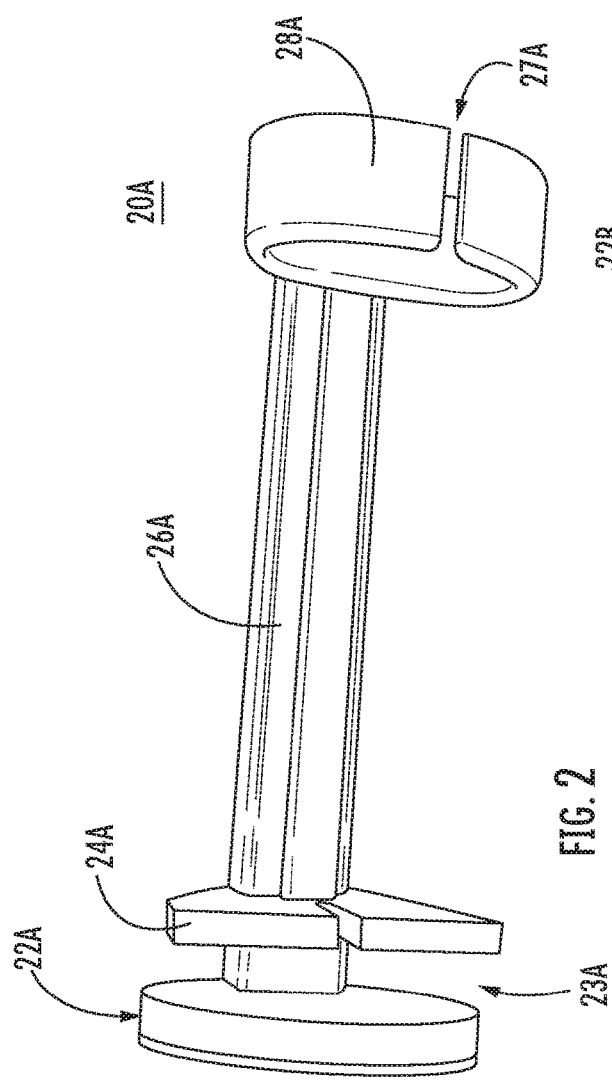
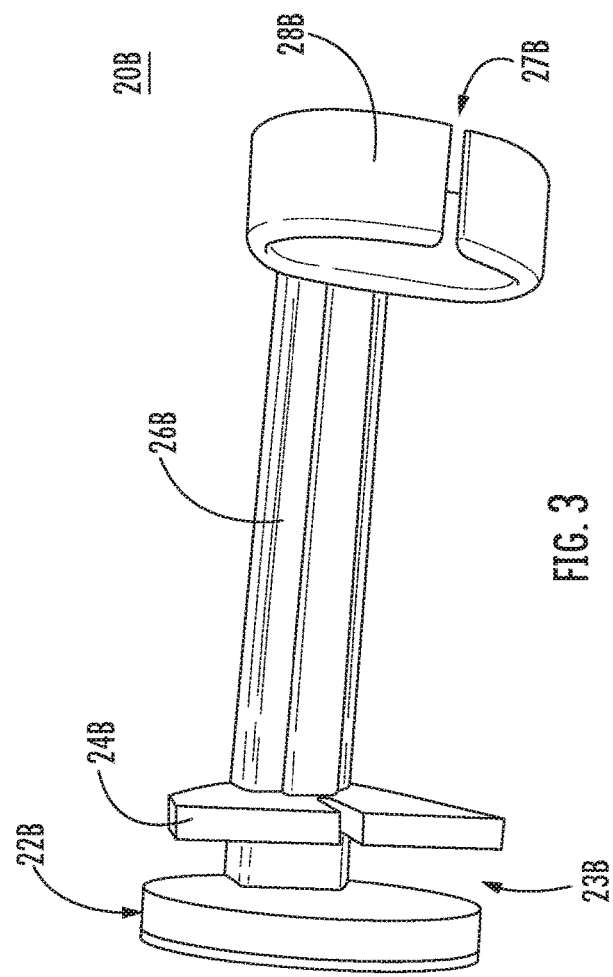

DOSAGE LIMITING DEVICE

FIELD

This invention relates to the field of medicine and more particularly to a system for limiting dosages administered by a syringe.

BACKGROUND

It is well known in the art of medicine to administer liquid medication using a syringe. For example, a small child may be given a dosage of 3 ml by way of a plastic syringe. The person or caregiver pushes the plunger of the syringe all the way in, then places the tip of the syringe into the liquid medication, then pulls the plunger out until the base of the plunger aligns with a gradient matching the dosage, or in this example, 3 ml. Then, the tip of the syringe is placed in the mouth of the child and the plunger of the syringe is pushed back in, delivering the requisite amount of the medicine.

Unfortunately, this method of administering a liquid medication (or any liquid) suffers from inaccuracies caused by many reason. For example, the caregiver (or person taking the medication) has poor visibility to the gradients due to darkness or poor eyesight or the caregiver does not understand how to correctly meter the dosage, etc. Due to such inaccuracies, the patient (receiver of the liquid) often is provided with too much of the liquid (medication) or too little.

What is needed is a system that will meter the dosage provided from a syringe to the amount required.

SUMMARY

In one embodiment, a dosage limiting device is disclosed including an elongated connecting member having a plunger receiving head at a first end for capturing a plunger flange of a plunger of a syringe. A barrel loop is at a distal second end of the elongated connecting member. The dosage limiting device limits a dosage provided by the syringe based upon a distance between the plunger receiving head and the barrel loop as the barrel loop abuts a barrel flange of the syringe as the plunger is pulled out of the hollow body of the syringe, thereby limiting extraction of the plunger of the syringe and therefore, the dosage.

In another embodiment, a method of limiting a dosage provided by a syringe is disclosed including installing a dosage limiting device on the syringe by installing a plunger receiving head of the dosage limiting device on a plunger flange of the syringe, the plunger receiving head at a first end of an elongated connecting member, and installing a barrel loop of the dosage limiting device around the hollow barrel of the syringe, the barrel loop at a distal second end of the elongated connecting member. Now, pushing the plunger flange of the syringe until the plunger of the syringe is fully within the hollow barrel of the syringe and submerging a hollow tip of the syringe into a liquid. Next, pulling the plunger flange of the syringe until the barrel loop abuts a barrel flange of the syringe, thereby filling the hollow body of the syringe with the liquid to a dosage limited by the dosage limiting device. Now, the hollow tip is placed into a destination (e.g. a mouth of a patient) and the plunger flange of the syringe is pushed into the syringe until the plunger of the syringe is fully within the hollow barrel of the syringe, thereby delivering the dosage limited by the dosage limiting device into the destination.

In another embodiment, a dosage limiting device is disclosed including an elongated connecting member that has a plunger receiving head at a first end for capturing a plunger flange of a plunger of a syringe. The plunger receiving head has a back flange connected to the elongated connecting member and a forward slotted flange connected to the elongated connecting member, the forward slotted flange is separated from the back flange by a space sufficient to accept the plunger flange and a flat section of the plunger fitting in a slot of the forward slotted flange. A barrel loop is at a distal second end of the elongated connecting member so that the dosage limiting device limits a dosage provided by the syringe based upon a distance between the plunger receiving head and the barrel loop as the barrel loop abuts a barrel flange of the syringe, thereby limiting extraction of the plunger.

BRIEF DESCRIPTION OF THE DRAWINGS

The invention can be best understood by those having ordinary skill in the art by reference to the following detailed description when considered in conjunction with the accompanying drawings in which:

FIG. 2 illustrates a perspective view of a dosage limiting device manufactured for a first dosage amount.

FIG. 3 illustrates a perspective view of a dosage limiting device manufactured for a second dosage amount.

DETAILED DESCRIPTION

Figure 1:
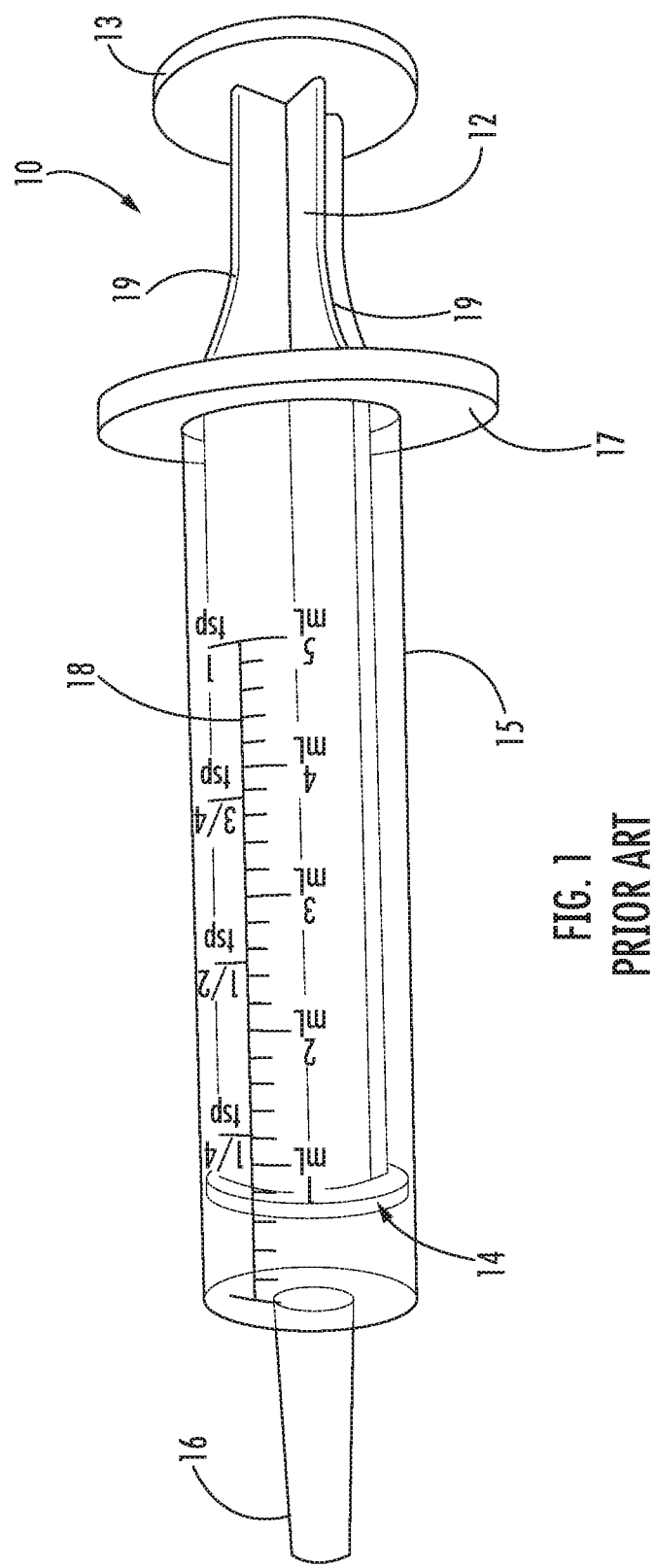
FIG. 1 illustrates a perspective view of a syringe of the prior art.
Figure 4:
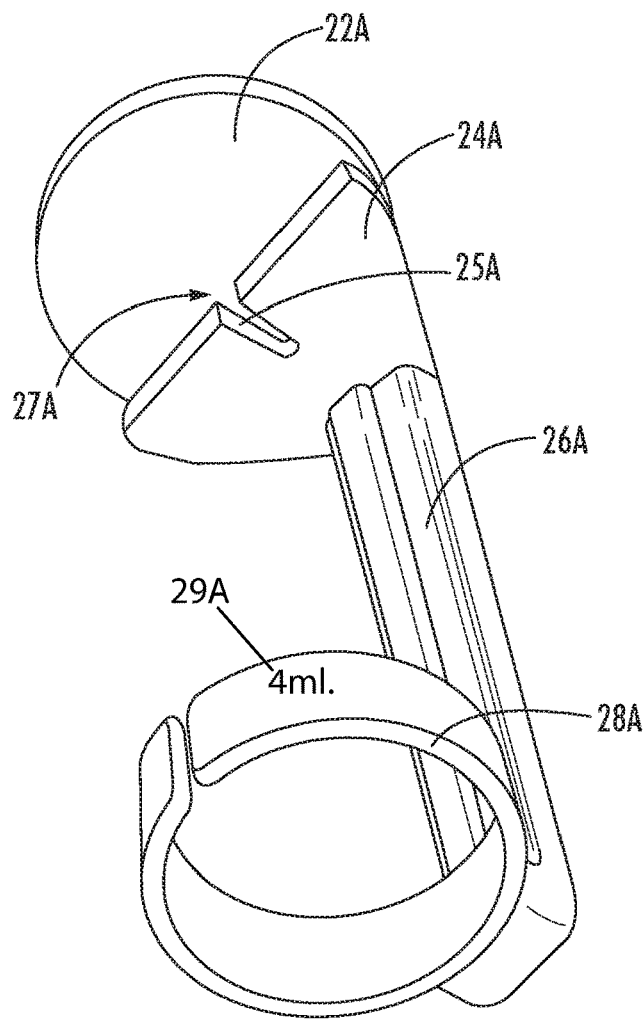
FIG. 4 illustrates a second perspective view of a dosage limiting device manufactured for the first dosage amount.
Figure 5:
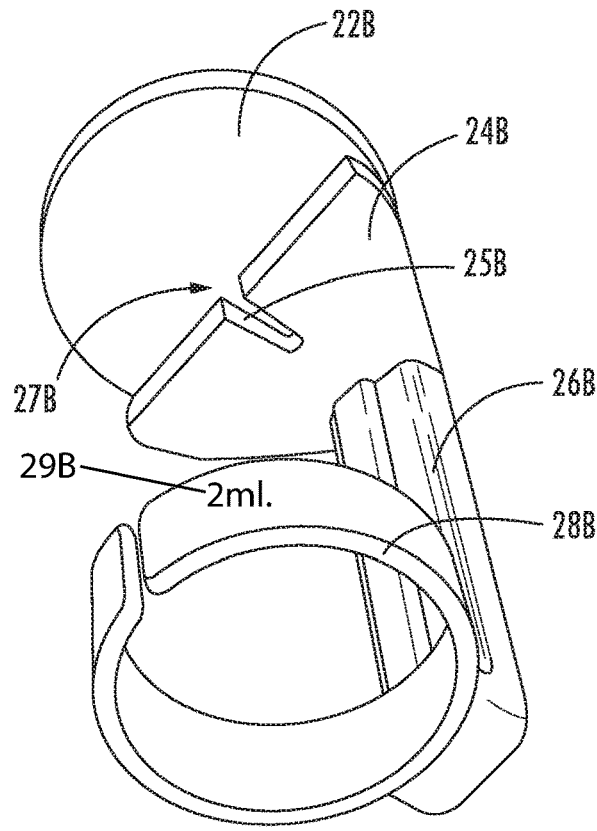
FIG. 5 illustrates a second perspective view of a dosage limiting device manufactured for the second dosage amount.

Reference will now be made in detail to the presently preferred embodiments of the invention, examples of which are illustrated in the accompanying drawings. Throughout the following detailed description, the same reference numerals refer to the same elements in all figures.

Referring to FIG. 1. An exemplary syringe 10 of the prior art is shown. The syringe 10 has a hollow tip 16 for drawing a liquid (e.g. medicine) into the hollow barrel 15 of the syringe 10 and, later, expelling the liquid into a destination (e.g. mouth of the patient). The liquid is drawn into the syringe 10 by first pushing the plunger flange 13 until the plunger seal 14 is all the way into the hollow barrel 15 of the syringe 10, then inserting the hollow tip 16 into the liquid, then pulling the plunger flange 13 out until the plunger seal 14 aligns with a gradient 18 matching the required dosage. To allow finger grips during operation, the syringe 10 has a barrel flange 17. The plunger 12 of a syringe 10 typically has flat sections 19 that improve rigidity.

In practice, syringes 10 provide a range of dosages, in that each typical syringe is capable of providing from a smallest dosage (e.g. 1 ml. or ¼ tsp.) to a largest dosage (e.g. 5 ml. or 1 tsp.).

Referring to FIGS. 2 through 9, two specific dosage limiting devices 20A/20B are shown. Although it is anticipated that dosage limiting devices 20A/20B be provided for any specific dosage, for clarity reasons, only two sizes of dosage limiting devices 20A/20B are shown in the figures and described. It should also be noted that the exact shape and composition of the two, specific dosage limiting devices 20A/20B is not limited as other shapes and materials will accomplish the same or similar function without veering from the disclosure and claims here within.

In FIGS. 2 through 5, the two specific dosage limiting devices 20A/20B are shown from the side. Each dosage limiting device 20A/20B has an elongated connecting member 26A/26B. At a first end of the elongated connecting members 26A/26B is a plunger flange receiving head 22A/24A/22B/24B for capturing a plunger flange 13 of the plunger 12 of the syringe 10. In the example shown, each plunger receiving head 22A/24A/22B/24B consists of a back flange 22A/22B and a forward slotted flange 24A/24B separated by a space 23A/23B wide enough to fit the plunger flange 13 of the plunger 12. The plunger flange 13 fits snuggly in the space between the back flange 22A/22B and a forward slotted flange 24A/24B. As the typical plunger 12 has flat sections 19 that improve rigidity, these flat sections 19 fit into the slot 25A/25B.

At a distal second end of the elongated connecting members 26A/26B is a barrel loop 26A/26B. As shown in FIGS. 6 through 9, in use, the hollow barrel 15 of the syringe 10 is inserted into the barrel loop 26A/26B and the plunger flange 13 of the syringe 10 is inserted into the plunger receiving head 22A/24A/22B/24B. The dosage limiting devices 20A/20B therefore limit the distance that the plunger flange 13 can be extracted from the hollow barrel 15 of the syringe as the barrel loop 26A/26B abuts the barrel flange 17 of the syringe 10.

In some embodiments, each barrel loop 26A/26B has a slit 27A/27B to facilitate capturing the hollow barrel 15 of the syringe 10 within the barrel loops 26A/26B. As one anticipated material from which the dosage limiting devices 20A/20B are made is plastic, by using a pliable and resilient plastic, the barrel loops 26A/26B will open at the slits 27A/27B for ease of installation onto the hollow barrel 15 of the syringe.

Note that the length of the elongated connecting member 26A/26B determines the dosage that is administered. For example, the first dosage limiting device 20A has a longer elongated connecting member 26A while the second dosage limiting device 20B has a shorter elongated connecting member 26B. Note that in some embodiments, the dosage limiting device 20A/20B is marked to indicate the dosage that will be administered using that dosage limiting device 20A/20B, for example, the dosage markings 29A (4 ml.) and 29B (2 ml.) shown in FIG. 3.

Figure 6:
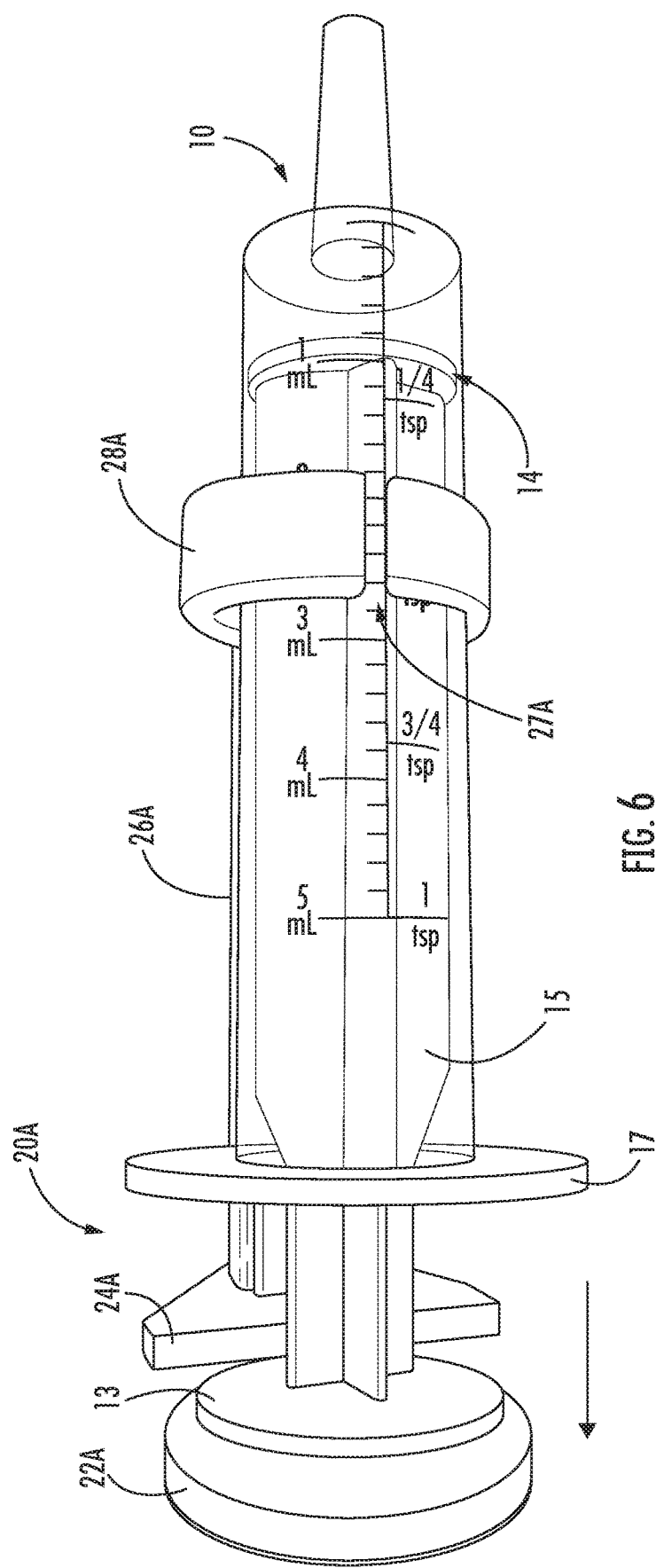
FIG. 6 illustrates a perspective view of a dosage limiting device manufactured for the first dosage amount installed on a syringe with the plunger pushed in all the way.
Figure 7:
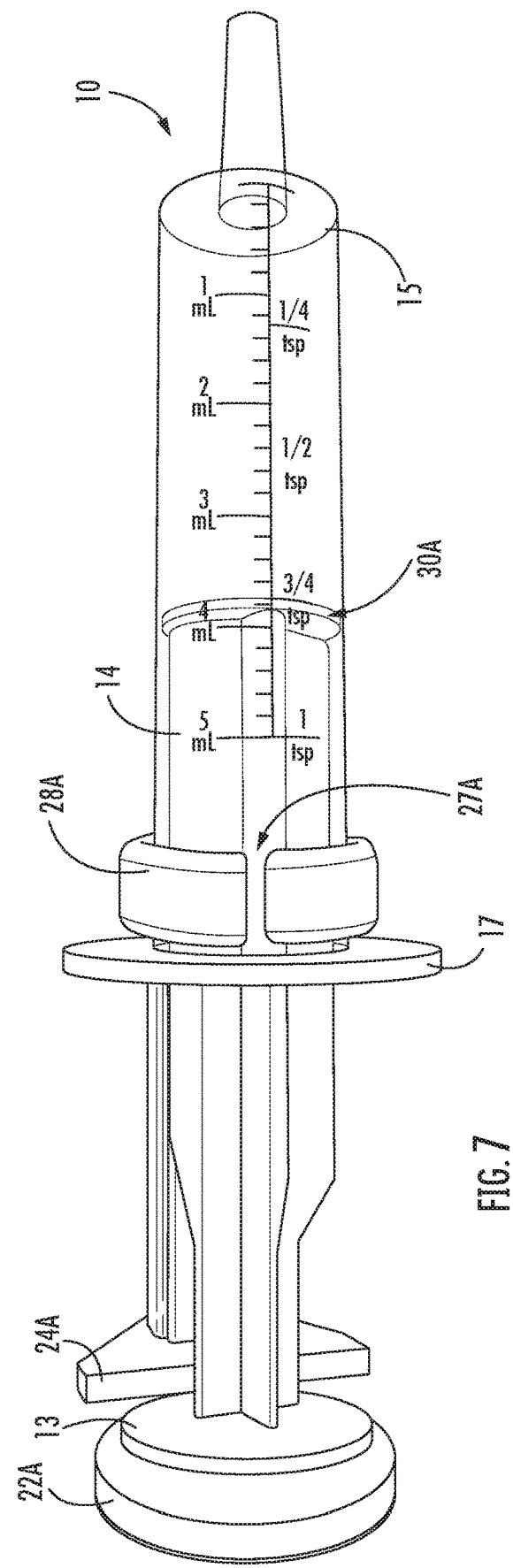
FIG. 7 illustrates a perspective view of a dosage limiting device manufactured for the first dosage amount installed on a syringe with the plunger pulled out as far as allowed by the dosage limiting device.

Operation of the dosage limiting devices 20A/20B are shown in FIGS. 6-9. In FIG. 6, the first dosage limiting device 20A mounted on the syringe 10 with the plunger 12 of the syringe 10 pushed in. In FIG. 7, the first dosage limiting device 20A is shown limiting how far the plunger 12 of the syringe 10 can be pulled out. In this example, when the plunger 12 of the syringe 10 is pulled out, the first dosage limiting device 20A limits extraction to the ¾ tsp. gradient 30A, therefore, in this example, the first dosage limiting device 20A limits the dosage to ¾ tsp.

Figure 8:
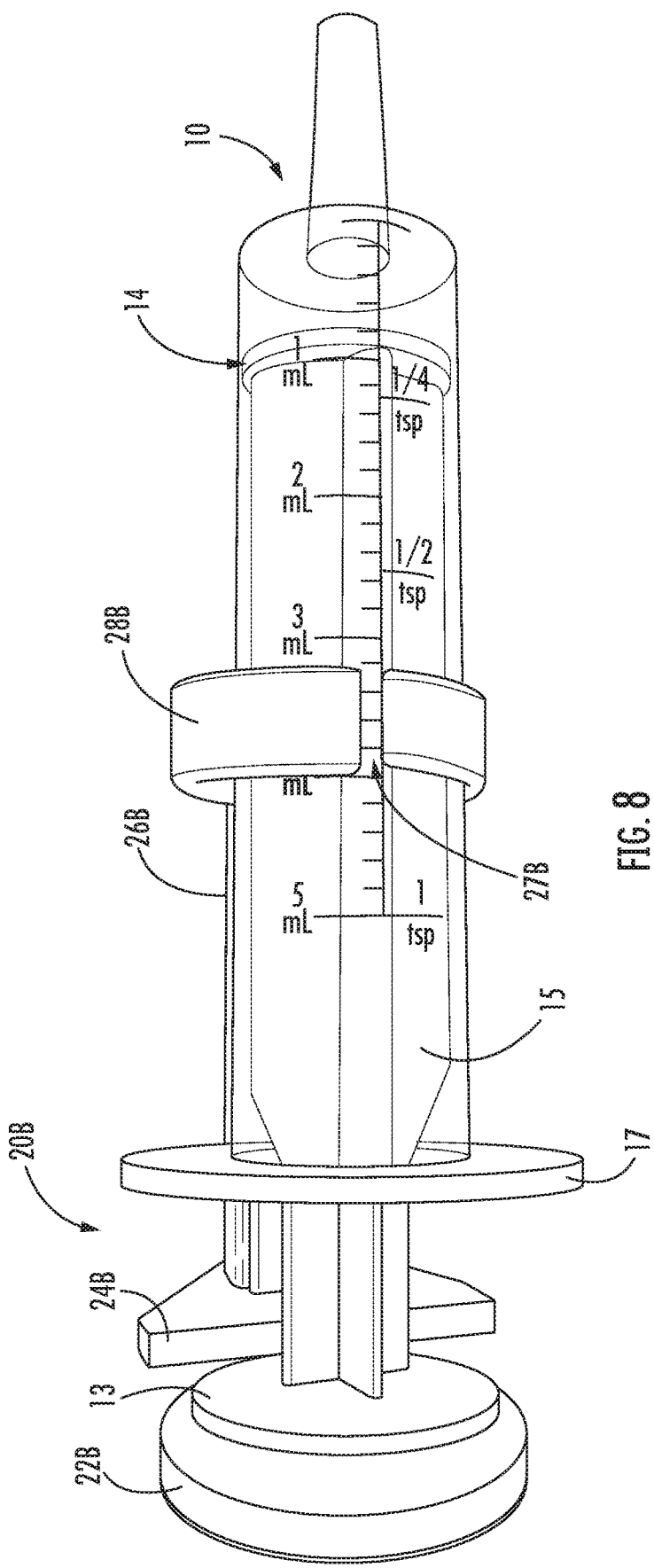
FIG. 8 illustrates a perspective view of a dosage limiting device manufactured for the second dosage amount installed on a syringe with the plunger pushed in all the way.
Figure 9:
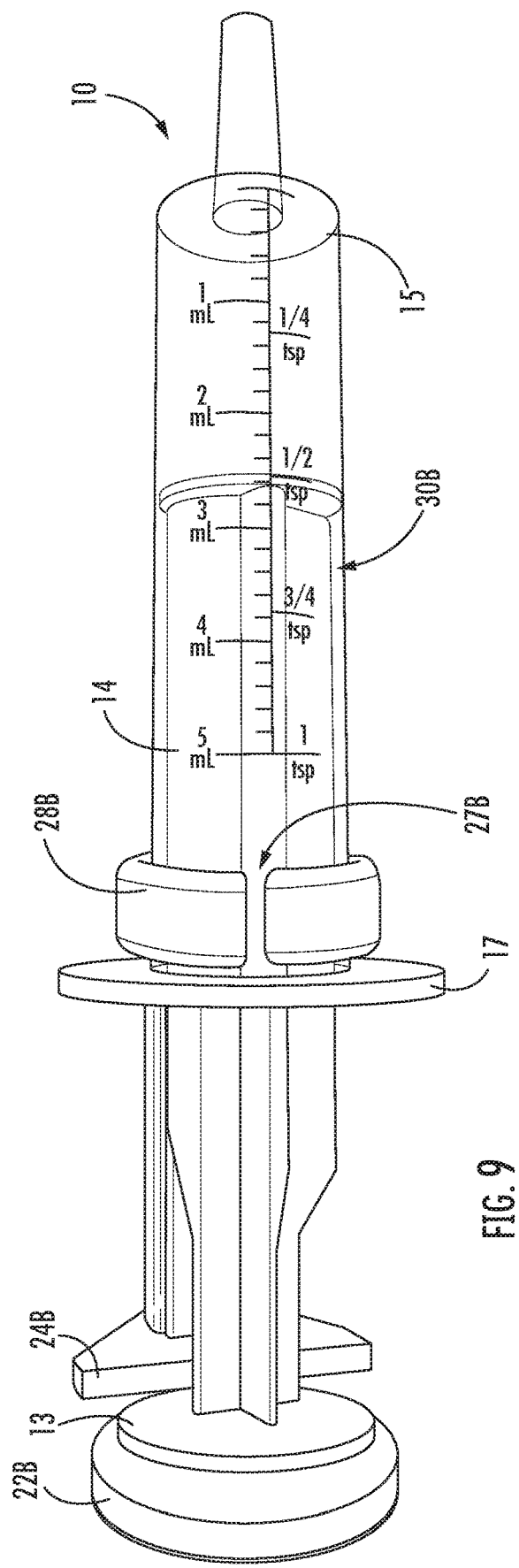
FIG. 9 illustrates a perspective view of a dosage limiting device manufactured for the second dosage amount installed on a syringe with the plunger pulled out as far as allowed by the dosage limiting device.

Now, in FIG. 8, the second dosage limiting device 20B is mounted on the syringe 10 with the plunger 12 of the syringe 10 pushed in. In FIG. 9, the second dosage limiting device 20B is shown limiting how far the plunger 12 of the syringe 10 can be pulled out. In this example, when the plunger 12 of the syringe 10 is pulled out, the second dosage limiting device 20B limits extraction to the ½ tsp. gradient 30B, therefore, in this example, the second dosage limiting device 20B limits the dosage to ½ tsp.

Again, the two dosage limiting devices 20A/20B are examples and it is fully anticipated that dosage limiting devices 20A/20B be provided for various sizes of syringes and for any desired dosage in metric (e.g. ml) or English units (e.g. tsp.).

It is fully anticipated that the dosage limiting devices 20A/20B be provided as single items or in packages containing several, either having all the same dosage amounts or different dosage amounts. For example, a package of five dosage limiting devices 20A/20B contains one each dosage limiting device 20A/20B or 1 ml, 2 ml, 3 ml, 4 ml, and 5 ml. It is also anticipated that, in some embodiments, each dosage limiting devices 20A/20B be marked with markings indicating the dosage of such and, in some embodiments a company advertisement is also marked on the dosage limiting devices 20A/20B (e.g., a pharmacy name).

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A method of limiting a dosage provided by a syringe, the method comprising:
installing a dosage limiting device on the syringe by:
installing a plunger receiving head of the dosage limiting device on a plunger flange of the syringe, the plunger receiving head at a first end of an elongated connecting member;
installing a barrel loop of the dosage limiting device around a hollow barrel of the syringe, the barrel loop being fixed at a distal second end of the elongated connecting member;
pushing the plunger flange of the syringe until the plunger of the syringe is fully within the hollow barrel of the syringe;
submerging a hollow tip of the syringe into a liquid;
pulling the plunger flange of the syringe until the barrel loop abuts a barrel flange of the syringe, thereby filling a portion of the hollow barrel of the syringe with the liquid to a dosage limited by the dosage limiting device;
placing the hollow tip into a destination;
pushing the plunger flange of the syringe until the plunger of the syringe is fully within the hollow barrel of the syringe, thereby delivering the dosage limited by the dosage limiting device into the destination.

2. The method of claim 1, wherein the plunger receiving head has a back flange connected to the elongated connecting member and a forward slotted flange connected to the elongated connecting member, forward slotted flange is separated from the back flange by a space sufficient to accept the plunger flange, a flat section of the plunger fitting in a slot of the forward slotted flange.

3. The method of claim 1, wherein the barrel loop of the dosage limiting device is tubular to surround the hollow barrel of the syringe.

4. The method of claim 3, wherein the barrel loop has a slit for ease of installation on the hollow barrel of the syringe.

5. The method of claim 1, further comprising markings on the elongated connecting member of the dosage limiting device.

6. The method of claim 5, wherein the markings include a dosage amount.

7. The method of claim 1, further comprising an advertisement on the elongated connecting member of the dosage limiting device and the method further comprising subsidizing a cost of the dosage limiting device through an advertiser paying for the advertisement.

8. A dosage limiting device comprising:
an elongated connecting member;
a plunger receiving head for capturing a plunger flange of a plunger of a syringe, the plunger receiving head is at a first end of the elongated connecting member, the plunger receiving head has a back flange connected to the elongated connecting member and a forward slotted flange connected to the elongated connecting member, the forward slotted flange is separated from the back flange by a space sufficient to accept the plunger flange, a flat section of the plunger fitting in a slot of the forward slotted flange; and
a barrel loop fixed at a distal second end of the elongated connecting member;
whereas the dosage limiting device limits a dosage provided by the syringe based upon a distance between the plunger receiving head and the barrel loop as the barrel loop abuts a barrel flange of the syringe, thereby limiting extraction of the plunger.

9. The dosage limiting device of claim 8, wherein the barrel loop is tubular to surround a hollow barrel of the syringe.

10. The dosage limiting device of claim 9, wherein the barrel loop has a slit for ease of installation on the hollow barrel of the syringe.

11. The dosage limiting device of claim 8, further comprising markings on the elongated connecting member.

12. The dosage limiting device of claim 11, wherein the markings include a dosage amount.

13. The dosage limiting device of claim 11, wherein the markings include an advertisement.

* * * * *